(12) United States Patent
Gou et al.

(10) Patent No.: US 11,865,367 B2
(45) Date of Patent: Jan. 9, 2024

(54) SETUP METHOD AND APPARATUS, DATA PROCESSING DEVICE, AND RADIOTHERAPY SYSTEM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Tianchang Gou, Xi'an (CN); Hao Yan, Xi'an (CN); Jinsheng Li, Xi'an (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 757 days.

(21) Appl. No.: 17/040,013

(22) PCT Filed: Mar. 18, 2019

(86) PCT No.: PCT/CN2019/078434
§ 371 (c)(1),
(2) Date: Sep. 21, 2020

(87) PCT Pub. No.: WO2019/179383
PCT Pub. Date: Sep. 26, 2019

(65) Prior Publication Data
US 2021/0016110 A1    Jan. 21, 2021

(30) Foreign Application Priority Data

Mar. 21, 2018  (CN) .......................... 201810235211.1

(51) Int. Cl.
*A61N 5/10* (2006.01)
*A61B 90/00* (2016.01)

(52) U.S. Cl.
CPC ............ *A61N 5/1049* (2013.01); *A61B 90/39* (2016.02); *A61B 2090/3937* (2016.02); *A61N 2005/1056* (2013.01); *A61N 2005/1059* (2013.01)

(58) Field of Classification Search
CPC ............ A61B 90/39; A61B 2090/3937; A61N 5/1049; A61N 2005/1056; A61N 2005/1059; A61N 2005/1097
See application file for complete search history.

(56) References Cited

U.S. PATENT DOCUMENTS 7,166,852 B2 * 1/2007 Saracen ............... A61N 5/1049
250/491.1
2016/0023019 A1    1/2016 Filiberti et al.

FOREIGN PATENT DOCUMENTS

| CN | 2676831 Y | 2/2005 |
| CN | 106139414 A | 11/2016 |
| CN | 108635681 A | 10/2018 |

OTHER PUBLICATIONS

International Search Report and Written Opinion of corresponding PCT Application PCT/CN2019/078434—18 pages (dated May 31, 2019).

(Continued)

*Primary Examiner* — Mark R Gaworecki
(74) *Attorney, Agent, or Firm* — Knobbe, Martens, Olson & Bear, LLP

(57) ABSTRACT

Provided is a setup method which can include: acquiring a position of a reference mark point provided on a noninvasive positioning device in an infrared coordinate system of an infrared positioning system; according to the position of the reference mark point in the infrared coordinate system, a relative position between the reference mark point and an image center point in an electronic scanning image, and a position of an isocenter of a radiotherapy equipment in a (Continued)

patient supporting device PSD coordinate system of the radiotherapy equipment, determining a first offset between the image center point and the isocenter in the PSD coordinate system; and adjusting the first offset to a first target offset by adjusting a position of a patient supporting device in the PSD coordinate system.

20 Claims, 5 Drawing Sheets

(56) References Cited

OTHER PUBLICATIONS

Yu et al., "Development of Automated Real-Time Tracking and Localizing System in Radiotherapy", Chinese Medical Equipment Journal, vol. 29, No. 11—11 pages (Nov. 30, 2008).
First Office Action of corresponding Chinese Application No. 201810235211.1—16 pages (dated Sep. 30, 2019).
Second Office Action of corresponding Chinese Application No. 201810235211.1—9 pages (dated Apr. 8, 2020).
Notification to Grant Patent Right for Invention of corresponding Chinese application No. 201810235211.1—5 pages (dated Aug. 12, 2020).

* cited by examiner

SETUP METHOD AND APPARATUS, DATA PROCESSING DEVICE, AND RADIOTHERAPY SYSTEM

The present application is a national phase application of PCT Application No. PCT/CN2019/078434 filed on Mar. 18, 2019, which claims priority to Chinese Patent Application No. 201810235211.1, filed on Mar. 21, 2018 and entitled "SETUP METHOD AND APPARATUS, HOST COMPUTER, AND RADIOTHERAPY SYSTEM", the contents of which are incorporated herein by reference in their entireties.

TECHNICAL FIELD

The present disclosure relates to the field of radiotherapy, particularly, relates to a setup method and apparatus, a host computer, and a radiotherapy system.

BACKGROUND

Prior to a radiotherapy, the treatment couch needs to be moved, so as to arrange the position of the patient in such a way that a target in an affected part of the patient is aligned with the isocenter of radiotherapy equipment, thereby ensuring the precision of the radiotherapy. Here, the isocenter is a point where a beam focus of a radiation source of the radiotherapy equipment is located in a treatment chamber after the beam focus is adjusted to meet the axis of the treatment chamber of the radiotherapy equipment.

In the related art, a positioning head frame or an image guiding radiation therapy (IGRT) system is usually adopted in arranging the position of the patient. In the case of the positioning head frame, the affected part of the patient is fixed to the frame through a fixation pin, and then the affected part is further fixed to a predetermined position of the treatment couch through an adapter connected to the positioning head frame. In the case of the IGRT system, IGRT images of the affected part are acquired in real time during the procedure of arranging the position, and based on the IGRT images, offsets between the affected part and the isocenter can be determined, such that the position of the treatment couch can be adjusted according to the offsets, and the position of the patient can be arranged.

SUMMARY

Embodiments of the present disclosure provide a setup method and apparatus, a host computer, and a radiotherapy system. The technical solutions are as follows.

In one aspect, a setup method is provided. The method includes:
  acquiring, at a setup stage, a position of a reference mark point provided on a noninvasive positioning device in an infrared coordinate system of an infrared positioning system;
  according to the position of the reference mark point in the infrared coordinate system, a relative position between the reference mark point and an image center point in an electronic scanning image, and a position of an isocenter of a radiotherapy equipment in a patient supporting device (PSD) coordinate system of the radiotherapy equipment, determining a first offset between the image center point and the isocenter in the PSD coordinate system; and
  adjusting the first offset to a first target offset by adjusting a position of a patient supporting device in the PSD coordinate system.

Optionally, determining the first offset between the image center point and the isocenter in the PSD coordinate system according to the position of the reference mark point in the infrared coordinate system, the relative position between the reference mark point and the image center point in the electronic scanning image, and the position of the isocenter of a radiotherapy equipment in the PSD coordinate system of the radiotherapy equipment includes:
  determining the position of the image center point in the infrared coordinate system, according to the position of the reference mark point in the infrared coordinate system, and the relative position between the reference mark point and the image center point in the electronic scanning image; and
  determining the first offset between the image center point and the isocenter in the PSD coordinate system based on the position of the image center point in the infrared coordinate system, the position of the isocenter of the radiotherapy equipment in the PSD coordinate system of the radiotherapy equipment, and a conversion relationship between the infrared coordinate system and the PSD coordinate system.

Optionally, determining the first offset between the image center point and the isocenter in the PSD coordinate system based on the position of the image center point in the infrared coordinate system, the position of the isocenter of the radiotherapy equipment in the PSD coordinate system of the radiotherapy equipment, and the conversion relationship between the infrared coordinate system and the PSD coordinate system includes:
  determining a position of the image center point in the PSD coordinate system according to the position of the image center point in the infrared coordinate system and the conversion relationship between the infrared coordinate system and the PSD coordinate system; and
  determining the first offset between the image center point and the isocenter in the PSD coordinate system based on the position of the image center point in the PSD coordinate system and the position of the isocenter in the PSD coordinate system.

Optionally, the method further includes:
  acquiring, at the setup stage, a position of a positioning mark point provided on a body surface of a patient in the infrared coordinate system;
  determining a first relative position between the positioning mark point and the reference mark point in the infrared coordinate system;
  determining a second offset between the first relative position and a standard position in the PSD coordinate system according to a conversion relationship between the infrared coordinate system and the PSD coordinate system, wherein the standard position is a relative position between the positioning mark point and the reference mark point in the electronic scanning image; and
  adjusting the second offset to a second target offset by adjusting the position of the patient supporting device in the PSD coordinate system.

Optionally, a plurality of positioning mark points are provided on the body surface of the patient;
  wherein determining the first relative position between the positioning mark point and the reference mark point in the infrared coordinate system includes:

determining the respective first relative position between each of the positioning mark points and the reference mark point in the infrared coordinate system, and obtaining a plurality of first relative positions;

wherein determining the second offset between the first relative position and the standard position in the PSD coordinate system includes:

determining the respective second offset between each of the first relative positions and the standard position in the PSD coordinate system according to the conversion relationship between the infrared coordinate system and the PSD coordinate system, and obtaining a plurality of second offsets; and wherein adjusting the second offset to the second target offset by adjusting the position of the patient supporting device includes:

detecting each of the second offsets for whether it is within a target offset range; and when it is determined that a number of second offsets that are not within the target offset range is more than a number threshold, adjusting the second offsets to the second target offset by adjusting the position of the patient supporting device.

Optionally, the noninvasive positioning device includes a positioning mask and a positioning bracket for fixing the positioning mask; and wherein at least one reference mark point is provided on at least one of the positioning mask and the positioning bracket.

Optionally, at least three reference mark points are provided on the noninvasive positioning device; and wherein among the at least three reference mark points, orthographic projections of any two reference mark points onto a first plane are not overlapped, the first plane being a plane defined by any two coordinate axes in the PSD coordinate system.

In another aspect, a setup apparatus is provided. The apparatus includes:

a first acquisition module configured to acquire, at a setup stage, a position of a reference mark point provided on a noninvasive positioning device in an infrared coordinate system of an infrared positioning system;

a first determination module configured to determine, according to the position of the reference mark point in the infrared coordinate system, a relative position between the reference mark point and an image center point in an electronic scanning image, and a position of an isocenter of a radiotherapy equipment in a PSD coordinate system of the radiotherapy equipment, a first offset between the image center point and the isocenter in the PSD coordinate system; and an adjustment module configured to adjust the first offset to a first target offset by adjusting a position of a patient supporting device in the PSD coordinate system.

In yet another aspect, a data processing device is provided. The host computer includes a memory, a processor, and a computer program stored in the memory and executable by the processor, wherein the computer program, when executed by the processor, performs the setup method as defined in the first aspect.

In yet still another aspect, a radiotherapy system is provided. The radiotherapy system includes an infrared positioning system, a patient supporting device, and the data processing device as defined in the above aspect.

In yet another aspect, a non-volatile computer-readable storage medium is provided. The non-volatile computer-readable storage medium has instructions stored thereon, wherein the non-volatile computer-readable storage medium, when run on a computer, causes the computer to perform the setup method as defined in the above aspect.

BRIEF DESCRIPTION OF DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and those persons of ordinary skill in the art may also derive other drawings from these accompanying drawings without creative efforts.

DESCRIPTION OF EMBODIMENTS

For clearer descriptions of the objectives, technical solutions, and advantages of the present disclosure, some embodiments of the present disclosure are further described in detail in combination with the accompanying drawings.

Figure 1:
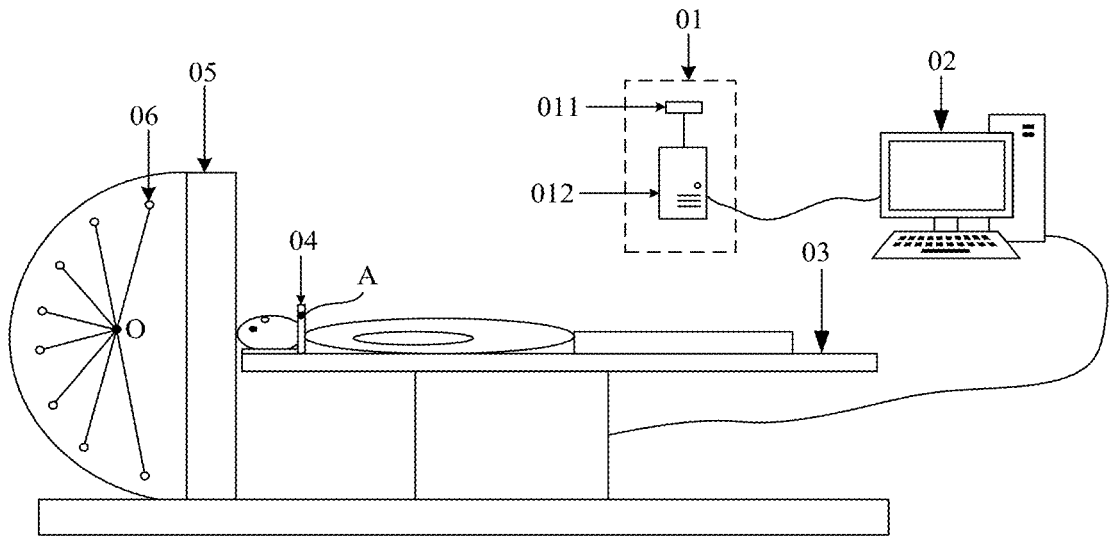
FIG. 1 is a schematic structural diagram of a radiotherapy system according to an embodiment of the present disclosure.

FIG. 1 is a schematic structural diagram of a radiotherapy system according to an embodiment of the present disclosure. As shown in FIG. 1, the radiotherapy system may include an infrared positioning system 01, a host computer 02, a patient supporting device 03, and a noninvasive positioning device 04. The noninvasive positioning device 04 may be arranged on the patient supporting device 03, and a reference mark point A may be provided on the noninvasive positioning device 04.

The infrared positioning system 01 may be arranged above the patient supporting device 03. The host computer 02 is respectively connected to the infrared positioning system 01 and the patient supporting device 03. When conducting a radiotherapy, a positioning mark point may be provided on a body surface of a patient. The infrared positioning system 01 may detect the position of the reference mark point A and the position of the positioning mark point during the process of radiotherapy. Further, the infrared positioning system 01 may determine an offset of the patient supporting device 03 according to the detected positions. After that, the infrared positioning system 01 may send the offset to the host computer 02. The host computer 02 can adjust the position of the patient supporting device 03 according to the offset. Here, the host computer 02 may be a device such as a computer or a server having a data processing function. The patient supporting device 03 may be a treatment couch, a treatment chair or other devices for supporting and retaining the patient, as well as facilitating the setup of the patient. As used herein, the term "setup" includes the process of adjusting or arranging the position of a patient so as to place the patient in an appropriate position.

In the embodiments of the present disclosure, after the position of the reference mark point A and the position of the positioning mark point are detected by the infrared positioning system 01, the offset of the patient supporting device 03 can be further determined according to the positions detected by the infrared positioning system 01, and then whether the patient has moved, i.e., whether the position of the treatment couch needs to be adjusted, can be determined. Further, after determining that the patient has moved, the position of the treatment couch may be adjusted in a timely manner to re-position the patient. As such, the radiotherapy system have a variety of functions, and the movement of the patient would not have an influence on the treatment precision, thereby improving the precision of radiotherapy.

Optionally, as shown in FIG. 1, the infrared positioning system 01 may include an infrared detection module 011. The detection range of the infrared detection module 011 can cover the areas where the reference mark point A and the positioning mark point are located. The infrared detection module 011 can emit detection light to detect the positions of the positioning mark point and the reference mark point in an infrared coordinate system.

Optionally, as shown in FIG. 1, the infrared positioning system 01 may further include a processing module 012. The processing module 012 can be respectively connected to the infrared detection module 011 and the host computer 02. For example, the processing module 012 may establish a connection with other devices over a wired network or a wireless network. The infrared detection module 011 may send the detected positions to the processing module 012. The processing module 012 may send the positions to the host computer 02, so that the host computer 02 can determine the offset according to the positions, and further adjust the position of the patient supporting device according to the determined offset. In this way, an automatic control on the patient supporting device can be realized, thereby improving the efficiency of setup and radiotherapy.

It can be seen from FIG. 1 that the radiotherapy system may further include a treatment gantry 05. The treatment gantry 05 is provided with a plurality of radiation sources 06. Treatment beams emitted by the plurality of radiation sources 06 may intersect at a point O. This point is referred to as the beam focus. During the radiotherapy, the target point of an affected part of the patient is required to be aligned with the beam focus 0. As shown in FIG. 1, the infrared detection module 011 may be disposed above the patient supporting device 03 and opposite the treatment gantry 05.

Optionally, in the embodiment of the present disclosure, the infrared detection module 011 may include at least one infrared detector. The infrared detector can emit infrared ray, receive infrared ray reflected by positioning mark points and each reference mark point, and further determine positions of the positioning mark point and the reference mark point in the infrared coordinate system according to the received infrared ray. Correspondingly, an infrared reflective material that can effectively reflect infrared ray can be coated on both the reference mark point provided on the noninvasive positioning device 04 and the positioning mark point provided on the body surface of the patient, so as to improve the precision in positioning the positioning mark point and the reference mark point by the infrared detector.

Optionally, the reference mark point and the positioning mark point may be spherical structures, which may be formed from a carbon fiber material, and the infrared reflective material can be coated on the surface of the carbon fiber material. The infrared reflective material may include at least one of carbon, graphite, oxide, and carbide. Each infrared detector may include an infrared emitter and a binocular camera. The infrared emitter can emit infrared ray, and the binocular camera can detect infrared ray reflected by reference mark points and positioning mark points. Each infrared detector can determine the positions of the reference mark points and the positioning mark points based on the binocular positioning principle.

Figure 2:
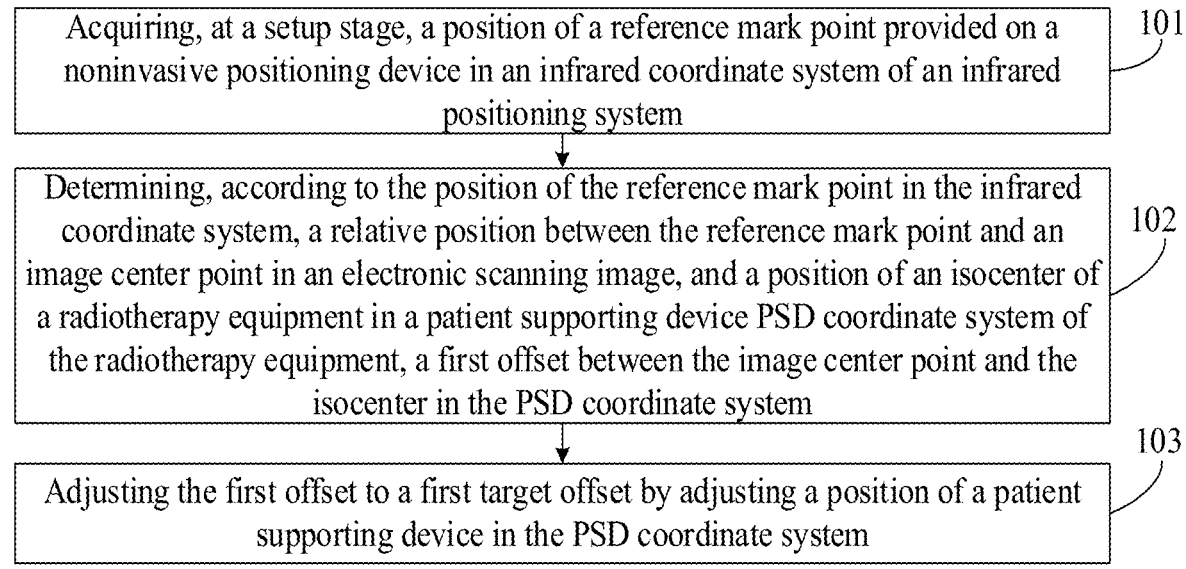
FIG. 2 is a flowchart showing a setup method according to an embodiment of the present disclosure.

FIG. 2 is a flowchart showing a setup method according to an embodiment of the present disclosure. The method is applicable to the host computer 02 shown in FIG. 1. Referring to FIG. 2, the method may include the following steps.

In step 101, a position of a reference mark point provided on a noninvasive positioning device in an infrared coordinate system of an infrared positioning system is acquired at a setup stage.

In the embodiment of the present disclosure, at the setup stage, the infrared positioning system may acquire the position of the reference mark point in the infrared coordinate system in real time and send the acquired position to the host computer.

In the case that the noninvasive positioning device is a head positioning device for fixing the head of a patient, the noninvasive positioning device may include a positioning mask and a positioning bracket for fixing the positioning mask. The reference mark point can be provided on the positioning mask or on the positioning bracket, or on both the positioning mask and the positioning bracket.

In step 102, according to the position of the reference mark point in the infrared coordinate system, a relative position between the reference mark point and an image center point in an electronic scanning image, and a position of an isocenter of a radiotherapy equipment in a patient supporting device (PSD) coordinate system of the radiotherapy equipment, a first offset between the image center point and the isocenter in the PSD coordinate system is determined.

The electronic scanning image may be an image obtained from a tomoscanner, and for example, may be a computed tomography (CT) image or a nuclear magnetic resonance image. The image center point may be a designated point in the electronic scanning image, for example, the image center point may be any point in the electronic scanning image designated in advance.

In step 103, the first offset is adjusted to a first target offset by adjusting the position of a patient supporting device in the PSD coordinate system.

In an embodiment of the present disclosure, the first target offset may be 0. As such, after the patient supporting device is adjusted by the host computer, the image center point can be aligned with the isocenter of the radiotherapy equipment. Alternatively, the first target offset may be a fixed value other than 0, and correspondingly, after the patient supporting device is adjusted by the host computer, a known relative positional relationship can be kept between the image center point and the isocenter.

In summary, in the setup method provided by the embodiments of the present disclosure, according to the position of the reference mark point provided on the noninvasive positioning device in the infrared coordinate system, the relative position between the reference mark point and the image center point in the electronic scanning image, and the position of the isocenter of the radiotherapy equipment in the PSD coordinate system of the radiotherapy equipment as acquired, the host computer can determine the first offset between the image center point and the isocenter of the radiotherapy equipment in the PSD coordinate system. Moreover, the first offset can be adjusted to the first target offset by adjusting the position of the patient supporting device, so as to realize the position arrangement of the patient. As such, an infrared positioning system is integrated into the method for arranging the position of the patient, the cost is low and no injure is brought to the patient.

Figure 3:
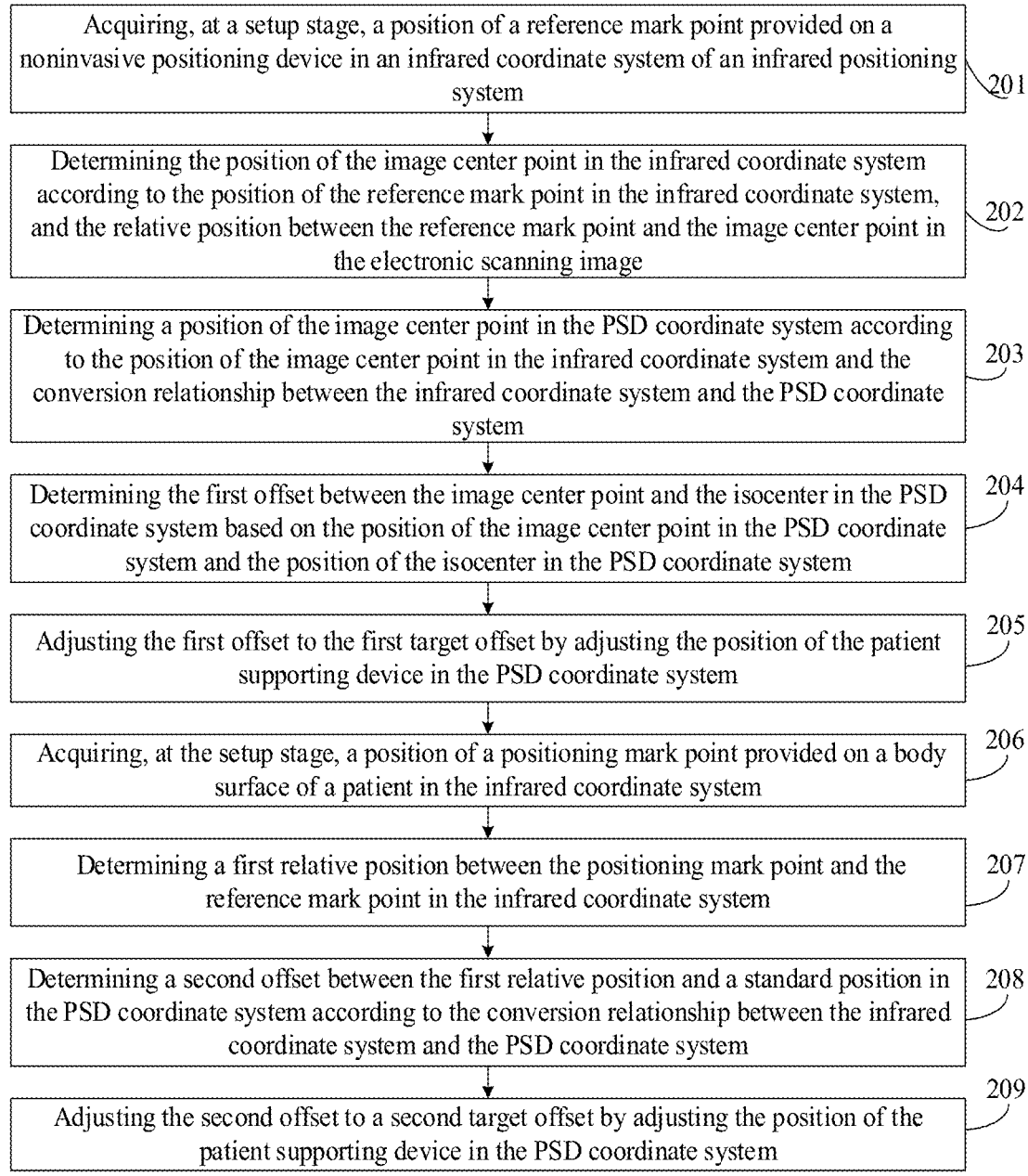
FIG. 3 is a flowchart showing another setup method according to an embodiment of the present disclosure.

FIG. 3 is a flowchart showing another setup method according to an embodiment of the present disclosure. The method is applicable to the host computer 02 shown in FIG. 1. Referring to FIG. 3, the method may include the following steps.

In step 201, a position of a reference mark point provided on a noninvasive positioning device in an infrared coordinate system of an infrared positioning system is acquired at a setup stage.

In the embodiment of the present disclosure, the host computer may acquire the position of the reference mark point acquired by the infrared positioning system. The noninvasive positioning device may include a positioning mask and a positioning bracket for fixing the positioning mask. At least one reference mark point can be provided on at least one of the positioning mask and the positioning bracket. That is, the at least one reference mark point may be disposed on the positioning mask or on the positioning bracket or on both the positioning mask and the positioning bracket.

To ensure the precision of the setup, at least three reference mark points can be provided on the noninvasive positioning device, and among the at least three reference mark points, orthographic projections of any two reference mark points onto a first plane are not overlapped, the first plane being a plane defined by any two coordinate axes of the PSD coordinate system.

For example, one reference mark point can be disposed on the positioning mask and two reference mark points can be disposed on the positioning bracket in advance. At the setup stage, the infrared positioning system can acquire respective position of each of the three reference mark points in the infrared coordinate system and send the position of each reference mark point to the host computer.

In step 202, according to the position of the reference mark point in the infrared coordinate system and a relative position between the reference mark point and an image center point in an electronic scanning image, a position of the image center point in the infrared coordinate system is determined.

In the embodiment of the present disclosure, at least one positioning mark point can be further provided on the body surface of the patient. After the positioning mark point and the reference mark point are disposed and before the setup stage is started (that is, during the formulation of a treatment plan), a tomoscanner (for example, a CT scanner or an NMR scanner) can be used to scan the affected part of the patient, to obtain the electronic scanning image of the affected part. Subsequently, any point in the electronic scanning image can be chosen as the image center point by the host computer, and then according to the image coordinate system defined by the electronic scanning image (referred to as a digital imaging and communications in medicine (DICOM) coordinate system), the relative position between the reference mark point and the image center point, and the position of the reference mark point in the infrared coordinate system, the host computer can determine the position of the image center point in the infrared coordinate system.

In the case that a plurality of reference mark points are provided on the noninvasive positioning device, in an optional implementation, the host computer may randomly choose a reference mark point as target reference mark point and determine, based on the position of the target reference mark point in the infrared coordinate system and a relative position between the target reference mark point and the image center point in the image coordinate system, the position of the image center point in the infrared coordinate system.

In an alternative implementation, the host computer may determine, based on the respective position of each reference mark point in the infrared coordinate system and the relative position between the reference mark point and the image center point in the image coordinate system, the respective image center point position in the infrared coordinate system, and therefore obtain a plurality of image center point positions. Subsequently, the host computer may calculate an average value of the plurality of image center point positions, and determine the average value as the position of the image center point in the infrared coordinate system.

In step 203, the position of the image center point in the PSD coordinate system is determined according to the position of the image center point in the infrared coordinate system and a conversion relationship between the infrared coordinate system and the PSD coordinate system.

In the embodiment of the present disclosure, the conversion relationship between the infrared coordinate system and the PSD coordinate system may be prestored in the host computer. The conversion relationship can be determined according to the position of the isocenter in the PSD coordinate system and the position of the isocenter in the infrared coordinate system. The position of the isocenter in the infrared coordinate system can be acquired by the host computer in advance. The conversion relationship may include a functional relationship between the position of each coordinate axis in the PSD coordinate system and the position of a corresponding coordinate axis in the infrared coordinate system. When converting a coordinate, the host computer may substitute the positional value of the image center point in the infrared coordinate system into the functional relationship, so as to obtain the positional value of the image center point in the PSD coordinate system.

As an example, the corresponding conversion relationship between the infrared coordinate system and the PSD coordinate system may follow the following formulas:

$$u = a_1 x + a_2 y + a_3 z$$

$$v = b_1 x + b_2 y + b_3 z$$

$$w = c_1 x + c_2 y + c_3 z \quad \text{Formula (1)},$$

where x, y, and z are respective coordinate values on each of the three coordinate axes in the infrared coordinate system, u, v, and w are respective coordinate values on each of the three coordinate axes in the PSD coordinate system, and a1 to a3, b1 to b3, and c1 to c3 are all predetermined conversion coefficients. When the position of an image center point in the infrared coordinate system, determined by the host computer, is (x1, y1, z1), then the host computer may further determine, according to formula (1), that the position of the image center point in the PSD coordinate system is (u1, v1, w1), where $u_1=a_1x_1+a_2y_1+a_3z_1$, $v_1=b_1x_1+b_2y_1+b_3z_1$, and $w_1=c_1x_1+c_2y_1+c_3z_1$.

In step 204, a first offset between the image center point and the isocenter in the PSD coordinate system is determined based on the position of the image center point in the PSD coordinate system and the position of the isocenter in the PSD coordinate system.

Further, the host computer may determine, according to the position of a predetermined isocenter of radiotherapy equipment in the PSD coordinate system and the position of the image center point in the PSD coordinate system, the first offset between the image center point and the isocenter in the PSD coordinate system.

As the PSD coordinate system is a three-dimensional coordinate system, the first offset is a three-dimensional offset. That is, the first offset may include three components, with each component indicating the offset of the patient supporting device on one coordinate axis of the PSD coordinate system.

Figure 4:
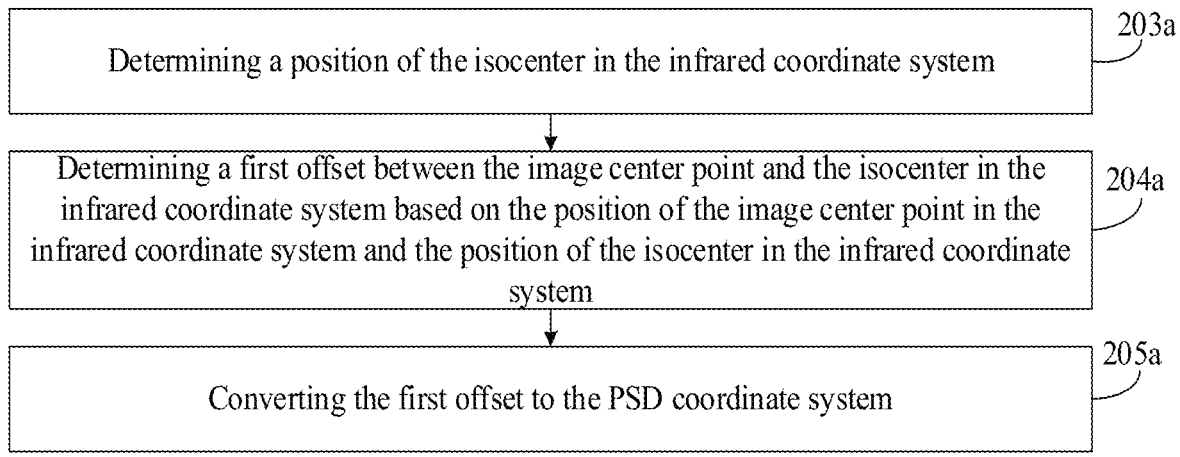
FIG. 4 is a flowchart showing a method for determining a first offset according to an embodiment of the present disclosure.

In an optional implementation of the embodiment of the present disclosure, after the above step 202, referring to FIG. 4, the host computer may also determine the first offset based on the position of the image center point in the infrared coordinate system via the following method.

In step 203a, the position of the isocenter in the infrared coordinate system is determined.

In the embodiment of the present disclosure, a mark point can be disposed at the isocenter in advance, and the infrared positioning system can acquire the position of the isocenter in the infrared coordinate system by detecting the position of the mark point and send the position to the host computer.

In step 204a, in the infrared coordinate system, a first offset between the image center point and the isocenter in the infrared coordinate system is determined based on the position of the image center point in the infrared coordinate system and the position of the isocenter in the infrared coordinate system.

Further, the host computer may calculate the first offset between the image center point and the isocenter in the infrared coordinate system.

In step 205a, the first offset in the infrared coordinate system is converted to a first offset in the PSD coordinate system.

Finally, the host computer may convert the first offset in the infrared coordinate system to a first offset in the PSD coordinate system according to the conversion relationship between the infrared coordinate system and the PSD coordinate system, so that the position of the patient supporting device can be adjusted according to the first offset in the PSD coordinate system.

In step 205, the first offset is adjusted to a first target offset by adjusting the position of the patient supporting device in the PSD coordinate system.

After the first offset between the image center point and the isocenter is determined by the host computer, the first offset can be adjusted to a first target offset by adjusting the position of the patient supporting device.

In the embodiment of the present disclosure, the first target offset may be an offset preset in the host computer. The first target offset may be 0, and correspondingly, the image center point can be aligned with the isocenter of the radiotherapy equipment after the patient supporting device is adjusted by the host computer. Alternatively, the first target offset may be a fixed value other than 0, and correspondingly, a known relative positional relationship can be kept between the image center point and the isocenter after the patient supporting device is adjusted by the host computer.

In the embodiment of the present disclosure, an initial position arrangement of the patient can be realized after the first offset is adjusted to the first target offset by the host computer. To ensure the accuracy of the setup, the host computer may continue to further conduct a precise setup on the patient. Continuing to refer to FIG. 3, the process of precise setup may include the following steps.

In step 206, a position of a positioning mark point provided on the body surface of the patient in the infrared coordinate system is acquired at the setup stage.

In the embodiment of the present disclosure, at least one positioning mark point may be provided on the body surface of the patient. For example, when conducting a radiotherapy on the head of the patient, at least one positioning mark point can be provided at the nasal bone of the patient. At the precise setup stage, the infrared positioning system may detect the position of each positioning mark point in the infrared coordinate system, and further send the detected position to the host computer.

In step 207, a first relative position between the positioning mark point and the reference mark point in the infrared coordinate system is determined.

Further, the first relative position can be calculated by the host computer according to the position of the reference mark point in the infrared coordinate system detected at the initial setup stage. Alternatively, the host computer may acquire, for a second time, the position of the reference mark point detected by the infrared positioning system at the precise setup stage, and calculate the first relative position between the positioning mark point and the reference mark point in the infrared coordinate system.

If a plurality of positioning mark points are provided on the body surface of the patient, the host computer may determine the respective first relative position between each positioning mark point and the reference mark point in the infrared coordinate system, so as to obtain a plurality of first relative positions that correspond to the plurality of positioning mark points in a one-to-one correspondence.

In the embodiment of the present disclosure, the first relative position corresponding to each positioning mark point may include the position of the positioning mark point and the position of each reference mark point. Alternatively, the first relative position corresponding to each positioning mark point may include vectors between the positioning mark point and each reference mark point. The position of the positioning mark point and the position of the reference mark point may be the positions thereof in the infrared coordinate system. Alternatively, the host computer may determine a reference origin based on the positioning mark point and the reference mark point (for example, any reference mark point or positioning mark point may be determined as the reference origin or a midpoint of a connecting line between two reference mark points may be determined as the reference origin), and then convert the infrared coordinate system based on the reference origin to obtain a converted coordinate system. The coordinates may alternatively indicate a position in the converted coordinate system.

In step 208, a second offset between the first relative position and a standard position in the PSD coordinate system is determined according to a conversion relationship between the infrared coordinate system and the PSD coordinate system.

The standard position is a relative position between the positioning mark point and the reference mark point in a pre-acquired electronic scanning image. That is, the standard position is a standard position in the image coordinate system.

In the embodiment of the present disclosure, the host computer may convert the first relative position relative to the PSD coordinate system according to the conversion relationship between the infrared coordinate system and the PSD coordinate system, and may further convert the standard position relative to the PSD coordinate system according to the conversion relationship between the image coordinate system and the PSD coordinate system. Subsequently, the second offset between the first relative position and the standard position in the PSD coordinate system can be calculated.

If a plurality of positioning mark points are provided on the body surface of the patient, then correspondingly, each positioning mark point would have one corresponding standard position. Referring to the foregoing description on the first relative position, the standard position corresponding to each positioning mark point may include: the position of the positioning mark point and each reference mark point in the image coordinate system. Alternatively, the standard position corresponding to each positioning mark point may include the positions of the positioning mark point and each reference mark point in the converted coordinate system (the coordinate system obtained after the conversion of the image coordinate system). Alternatively, the standard position corresponding to each positioning mark point may include vectors between the positioning mark point and each reference mark point.

Further, the host computer may determine the respective second offset between each first relative position and the corresponding standard position in the PSD coordinate system, and obtain a plurality of second offsets that correspond to the plurality of positioning mark points in a one-to-one correspondence.

When calculating the second offset corresponding to each positioning mark point, the host computer may first determine a first Euclidean distance between the positioning mark point and the reference mark point in the electronic scanning image in the PSD coordinate system according to the positions or vectors included in the standard position corresponding to the positioning mark point, and use the first Euclidean distance as a reference distance. Then, a second Euclidean distance between the positioning mark point and the reference mark point in the PSD coordinate system may be determined in the precise setup stage according to the positions or vectors included in the first relative position corresponding to the positioning mark point. The second Euclidean distance is an actually measured distance in the precise setup stage. Subsequently, the host computer may determine a difference value between the second Euclidean distance and the first Euclidean distance as the second offset corresponding to the positioning mark point.

If only one reference mark point is provided on the noninvasive positioning device, after a relative position between any positioning mark point and the reference mark point is acquired, the host computer can directly calculate the deviation between the relative position corresponding to the positioning mark point and a standard position corresponding to the positioning mark point. If a plurality of reference mark points are provided on the noninvasive positioning device, the first Euclidean distance corresponding to a positioning mark point may be an average value of Euclidean distances between the positioning mark point and each of the reference mark points.

At the precise setup process, the host computer may acquire the respective first relative position between the positioning mark point and each reference mark point; and after a plurality of first relative positions are obtained, a second Euclidean distance between the positioning mark point and each reference mark point may be determined based on the respective first relative position, so as to obtain a plurality of second Euclidean distances. Then, the host computer may respectively calculate an offset between each second Euclidean distance and the first Euclidean distance, so as to obtain a plurality of offsets. Subsequently, an average value of the plurality of offsets may be determined as the second offset corresponding to the positioning mark point. Alternatively, after calculating the plurality of second Euclidean distances, the host computer may first calculate an average value of the plurality of second Euclidean distances, and then calculate a difference value between the average value of the plurality of second Euclidean distances and the first Euclidean distance, so as to obtain the second offset.

For example, it is assumed that three positioning mark points B1, B2, and B3 are provided at the nasal bone of the patient, and two reference mark points A1 and A2 are provided on the noninvasive positioning device, then the first relative position, the standard position, and the second offset in the PSD coordinate system that are determined by the host computer may be those shown in Table 1.

TABLE 1

| Positioning mark point | First relative position | Standard position | Second offset |
| --- | --- | --- | --- |
| B1 | (B1, A1) (B1, A2) | (B1', A1')(B1', A2') | Δ1 |
| B2 | (B2, A1) (B2, A2) | (B2', A1')(B2', A2') | Δ2 |
| B3 | (B3, A1) (B3, A2) | (B3', A1')(B3', A2') | Δ3 |

As can be seen from Table 1, the positioning mark point B1 corresponds to two first relative positions. The two first relative positions are respectively the relative position between the positioning mark point B1 and the reference mark point A1 in the PSD coordinate system and the relative position between the positioning mark point B1 and the reference mark point A2 in the PSD coordinate system at the precise setup stage. Correspondingly, the host computer may acquire two standard positions corresponding to the positioning mark point B1 in advance. Respectively, the two standard positions includes the relative position between the positioning mark point BP (which is a same point as the positioning mark point B1) and the reference mark point A1' (which is a same point as the reference mark point A1) in the PSD coordinate system, and the relative position between the positioning mark point BP and the reference mark point A2' (which is a same point as the reference mark point A2) in the PSD coordinate system during electronic image scanning.

When calculating the second offset corresponding to the positioning mark point B1, the host computer may respectively calculate a Euclidean distance between B1' and A1' and a Euclidean distance between B1' and A2'. Then, the average value between the two Euclidean distances can be determined as the first Euclidean distance. Further, the host computer may respectively calculate a Euclidean distance between B1 and A1 and a Euclidean distance between B1 and A2, and obtain two second Euclidean distances. Finally, the host computer may determine a difference value between the average value of the two second Euclidean distances and the first Euclidean distance as a second offset A1 corresponding to the positioning mark point B1.

As to the positioning mark points B2 and B3, the host computer may also calculate second offsets Δ2 and Δ3 corresponding to each positioning mark point respectively by using the foregoing method, and three second offsets as shown in Table 1 can be eventually acquired.

In step 209, the second offset is adjusted to a second target offset by adjusting the position of the patient supporting device in the PSD coordinate system.

In the embodiment of the present disclosure, after acquiring the at least one second offset, the host computer may respectively detect whether each second offset is within a target offset range. If it is detected that a number of the second offsets that are not within the target offset range is more than a number threshold, it can be determined that the patient setup error is relatively large. Therefore, the second offset can be adjusted to the second target offset by adjusting the position of the patient supporting device. Otherwise, if it is detected that the number of the second offsets that are not within the target offset range is less than or equal to the target threshold, it can be determined that the patient setup precision meets the requirement and thus there is no need to adjust the position of the patient supporting device.

The target offset range may be determined in advance, and may be, for example, 0 mm to 3 mm. The number threshold may be a positive integer determined in advance according to the acquired number of the second offsets. For example, the number threshold may be one third of the number of the second offsets. Correspondingly, if the host computer detects three second offsets corresponding to three positioning mark points, then the number threshold may be 1. In this case, when detecting that the number of the second offsets that are not within the target offset range is more than 1, the host computer may determine that the position of the patient supporting device needs to be adjusted.

If the host computer detects that the number of the second offsets that are not within the target offset range is 0, it can be determined that the patient has not moved, and therefore there is no need to adjust the position of the patient supporting device.

In addition, if the host computer detects that the number of the second offsets that are not within the target offset range is 1, it can be determined that only a slight shift occurs, for instance, instead of the entire head of the patient in the positioning mask, only a certain position (for example, the eyebrow) of the head of the patient causes the positioning mark point at the nasal bone to shift. Therefore, the position of the patient supporting device does not need to be adjusted.

In the method provided by the embodiment of the present disclosure, when the mask does not deform, even if the head of the patient has a slight shift in the positioning mask, offsets of the positioning mark point provided at the nasal bone of the patient relative to the reference mark points on the noninvasive positioning device can be monitored, which in turn facilitates the adjustment on the position of the patient supporting device, thereby realizing a precise setup.

It needs to be noted that the second target offset recorded in this step may be the same as or may be different from the first target offset recorded in the step 205, which is not limited in this embodiment of the present disclosure.

It needs to be further noted that the setup method provided by the embodiment of the present disclosure makes the image center point align with the isocenter of the radiotherapy equipment or makes them keep a known relative positional relationship. In the electronic scanning image, as the target point(s) (there may be a plurality of target points) and the image center point have a fixed relative position, this relative position can be used in adjusting the position of the patient supporting device during the radiotherapy, so as to eventually align the target point(s) with the isocenter of the radiotherapy equipment.

Figure 5:
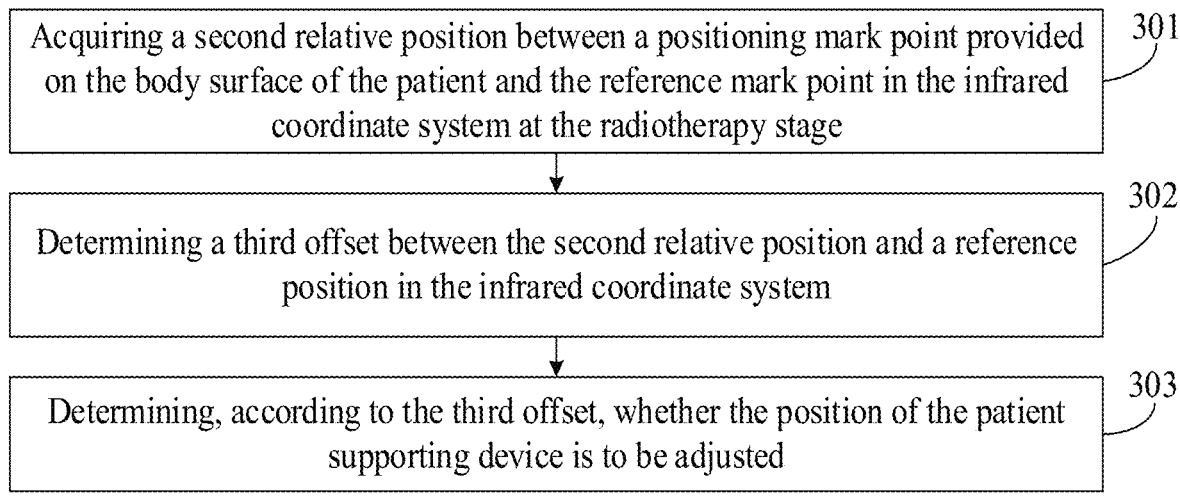
FIG. 5 is a flowchart showing a position detection method at a radiotherapy stage according to an embodiment of the present disclosure.

FIG. 5 is a flowchart showing a position detection method at a radiotherapy stage according to an embodiment of the present disclosure. The method is applicable to the host computer 02 as shown in FIG. 1. Referring to FIG. 5, the method may include the following steps.

In step 301, a second relative position between a positioning mark point provided on the body surface of a patient and a reference mark point in an infrared coordinate system is acquired at the radiotherapy stage.

In the embodiment of the present disclosure, at the radiotherapy stage, the infrared positioning system can periodically detect the position of the positioning mark point provided on the body surface of the patient and send the position to the host computer. The host computer may further calculate the second relative position between the positioning mark point and the reference mark point in the infrared coordinate system. If a plurality of positioning mark points are provided on the body surface of the patient, the host computer can respectively determine the second relative position between each positioning mark point and the reference mark point, so as to obtain a plurality of second relative positions.

Referring to the foregoing description on the first relative position, the respective second relative position corresponding to each positioning mark point may include the coordinates of the positioning mark point and each reference mark point in the infrared coordinate system. Alternatively, the respective second relative position may include the coordinates of the positioning mark point and each reference mark point in the converted coordinate system. Alternatively, the respective second relative position may include vectors between the positioning mark point and each reference mark point.

In step 302, a third offset between the second relative position and a reference position in the infrared coordinate system is determined.

The reference position may be a relative position between the positioning mark point and the reference mark point in the infrared coordinate system when a setup stage ends. If a plurality of positioning mark points are provided on the body surface of the patient, then correspondingly, the host computer can store a plurality of reference positions that correspond to the plurality of positioning mark points in a one-to-one correspondence.

Further, the host computer may determine the respective third offset between each second relative position and the corresponding reference position, and obtain a plurality of third offsets that correspond to the plurality of positioning mark points in a one-to-one correspondence. For the process of determining each third offset, reference can be made to the foregoing process of determining the second offset. Details are not described herein again.

In step 303, it is determined, according to the third offset, whether the position of the patient supporting device is to be adjusted.

In the embodiment of the present disclosure, after acquiring at least one third offset, the host computer may respectively detect whether each third offset is within a preset offset range.

If the host computer detects that a number of the third offsets that are not within the preset offset range is more than a preset number threshold, it can be determined that the patient setup error is relatively large, the radiotherapy needs to be interrupted, and the position of the patient supporting device can be adjusted based on the third offsets.

Otherwise, if the host computer detects that the number of third offsets that are not within the preset offset range is less than or equal to the preset number threshold, it can be determined that the patient setup precision meets the requirement, the radiotherapy may continue, and the position of the patient supporting device does not need to be adjusted.

It needs to be noted that the preset offset range used as a reference in this step may be the same as or may be different from the target offset range recorded in step 209. Similarly, the preset number threshold may be the same as or may be different from the number threshold recorded in step 209. This is not limited in this embodiment of the present disclosure.

In summary, in the setup method provided by the embodiments of the present disclosure, according to the position of the reference mark point provided on the noninvasive positioning device in the infrared coordinate system, the relative position between the reference mark point and the image center point in the electronic scanning image, and the position of the isocenter of the radiotherapy equipment in the PSD coordinate system of the radiotherapy equipment as acquired, the host computer can determine the first offset between the image center point and the isocenter of the radiotherapy equipment in the PSD coordinate system. Moreover, the first offset can be adjusted to the first target offset by adjusting the position of the patient supporting device, so as to realize the position arrangement of the patient. As such, an infrared positioning system is integrated into the method for arranging the position of the patient, the cost is low and no injure is brought to the patient.

It needs to be noted that the sequence of the steps of the setup method provided by the embodiment of the present disclosure may be appropriately adjusted, and the steps can be omitted or new steps can be added according to actual situation. For example, steps 205 to 209 may be deleted according to the situation. Any variant method that may be readily figured out by those skilled in the art within the technical scope disclosed in the present disclosure shall fall within the protection scope of the present disclosure. Therefore, details are not described again.

Figure 6:
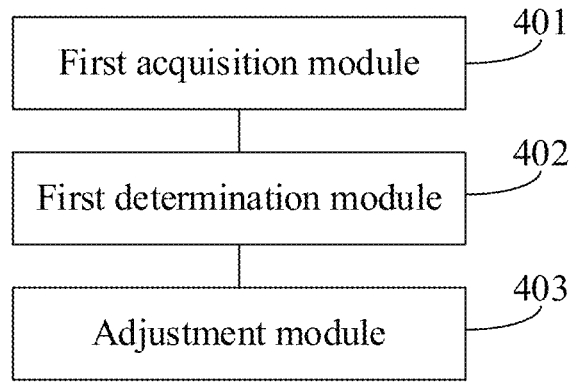
FIG. 6 is a schematic structural diagram of a setup apparatus according to an embodiment of the present disclosure.

FIG. 6 is a schematic structural diagram of a positioning apparatus according to an embodiment of the present disclosure. The apparatus is applicable to the host computer 02 as shown in FIG. 1. Referring to FIG. 6, the apparatus may include the following modules.

A first acquisition module 401 is configured to acquire, at a setup stage, a position of a reference mark point provided on a noninvasive positioning device in an infrared coordinate system of an infrared positioning system.

A first determination module 402 is configured to determine, according to the position of the reference mark point in the infrared coordinate system, a relative position between the reference mark point and an image center point in an electronic scanning image, and a position of an isocenter of a radiotherapy equipment in a patient supporting device PSD coordinate system of the radiotherapy equipment, a first offset between the image center point and the isocenter in the PSD coordinate system.

An adjustment module 403 is configured to adjust the first offset to a first target offset by adjusting a position of a patient supporting device in the PSD coordinate system.

Optionally, the first determination module 402 may include the following submodules.

A first determination submodule is configured to determine the position of the image center point in the infrared coordinate system according to the position of the reference mark point in the infrared coordinate system and the relative position between the reference mark point and the image center point in the electronic scanning image.

A second determination submodule is configured to determine the first offset between the image center point and the isocenter in the PSD coordinate system based on the position of the image center point in the infrared coordinate system, the position of the isocenter of the radiotherapy equipment in the PSD coordinate system of the radiotherapy equipment, and a conversion relationship between the infrared coordinate system and the PSD coordinate system.

Optionally, the second determination submodule may be further configured to:

determine a position of the image center point in the PSD coordinate system according to the position of the image center point in the infrared coordinate system and the conversion relationship between the infrared coordinate system and the PSD coordinate system; and determine the first offset between the image center point and the isocenter in the PSD coordinate system based on the position of the image center point in the PSD coordinate system and the position of the isocenter in the PSD coordinate system.

Figure 7:
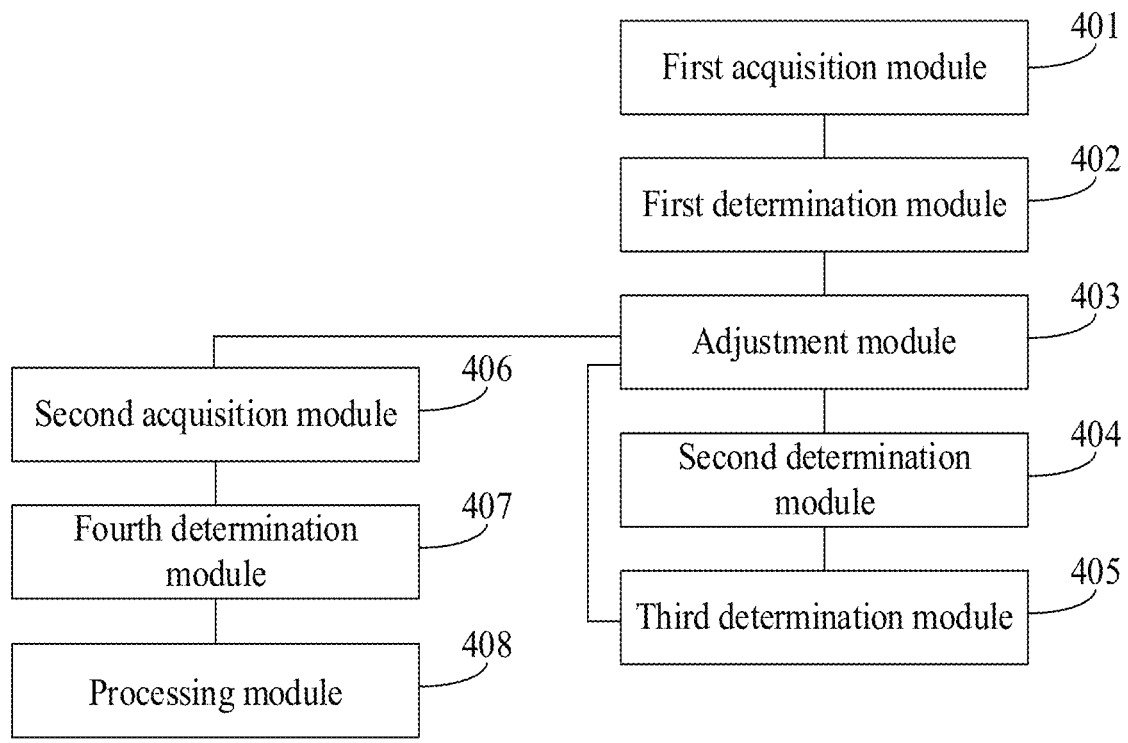
FIG. 7 is a schematic structural diagram of another setup apparatus according to an embodiment of the present disclosure.

Optionally, the first acquisition module 401 is further configured to acquire the position of a positioning mark point provided on the body surface of a patient in the infrared coordinate system at the setup stage. Referring to FIG. 7, the apparatus may further include the following modules.

A second determination module 404 is configured to determine a first relative position between the positioning mark point and the reference mark point in the infrared coordinate system.

A third determination module 405 is configured to determine a second offset between the first relative position and a standard position in the PSD coordinate system according to a conversion relationship between the infrared coordinate system and the PSD coordinate system. Here, the standard position is a relative position between the positioning mark point and the reference mark point in the electronic scanning image.

The adjustment module 403 is further configured to adjust the second offset to a second target offset by adjusting the position of the patient supporting device in the PSD coordinate system.

Optionally, a plurality of positioning mark points are provided on the body surface of the patient.

The second determination module 404 is configured to determine the respective first relative position between each of the positioning mark points and the reference mark point in the infrared coordinate system, and obtain a plurality of first relative positions.

The third determination module 405 is configured to determine the respective second offset between each of the first relative positions and the standard position in the PSD coordinate system according to the conversion relationship between the infrared coordinate system and the PSD coordinate system, and obtain a plurality of second offsets.

Correspondingly, the adjustment module 403 may be configured to:

detect each of the second offsets for whether it is within a target offset range, and adjust, when it is determined that a number of second offsets that are not within the target offset range is more than a number threshold, the second offsets to the second target offset by adjusting the position of the patient supporting device.

Optionally, as shown in FIG. 7, the apparatus may further include the following modules:

A second acquisition module 406 is configured to acquire a second relative position between a positioning mark point provided on the body surface of the patient and a reference mark point in the infrared coordinate system at the radiotherapy stage.

A fourth determination module 407 is configured to determine a third offset between the second relative position and a reference position in the infrared coordinate system. The reference position is a relative position between the positioning mark point and the reference mark point in the infrared coordinate system when the setup stage ends.

A processing module 408 is configured to determine, according to the third offset, whether the position of the patient supporting device is to be adjusted or not.

Optionally, the noninvasive positioning device includes a positioning mask and a positioning bracket for fixing the positioning mask, and at least one reference mark point is provided on at least one of the positioning mask and the positioning bracket.

Optionally, at least three reference mark points are provided on the noninvasive positioning device; and among the at least three reference mark points, orthographic projections of any two reference mark points onto a first plane are not overlapped, the first plane being a plane defined by any two coordinate axes in the PSD coordinate system.

In summary, in the setup apparatus provided by the embodiments of the present disclosure, after acquiring the position of the reference mark point provided on the noninvasive positioning device in the infrared coordinate system, the apparatus may further determine the position of the image center point of the electronic scanning image in the infrared coordinate system, then may determine the first offset between the image center point and the isocenter of the radiotherapy equipment in the PSD coordinate system based on the conversion relationship between the infrared coordinate system and the PSD coordinate system, and subsequently adjust the first offset to the first target offset by adjusting the position of the patient supporting device, so as to realize the position arrangement of the patient. As such, an infrared positioning system is integrated into the apparatus for arranging the position of the patient, the cost is low and no injure is brought to the patient.

It can be clearly understood by those skilled in the art that, for the purpose of convenient and brief description, for a detailed working process of the foregoing apparatuses and modules, reference can be made to the corresponding process in the foregoing method embodiments, and details are not described herein again.

Figure 8:
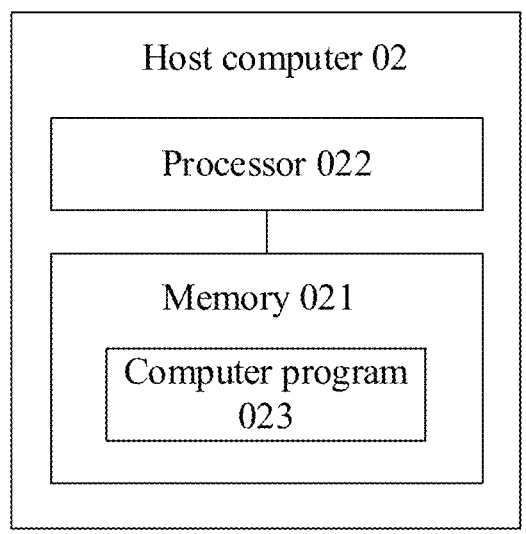
FIG. 8 is a schematic structural diagram of a host computer according to an embodiment of the present disclosure.

FIG. 8 is a schematic structural diagram of a host computer according to an embodiment of the present disclosure. Referring to FIG. 8, the host computer 02 may include a memory 021, a processor 022, and computer program(s) 023 that is/are stored in the memory 021 and may be run on the processor 022. The processor 022 executes the computer program(s) 023 to implement the setup method shown in FIG. 2 or FIG. 3 or the position detection method at the radiotherapy stage shown in FIG. 5.

An embodiment of the present disclosure provides a radiotherapy system. As shown in FIG. 1, the radiotherapy system may include an infrared positioning system 01, a patient supporting device 03, and a host computer 02.

The host computer 02 may include the setup apparatus shown in FIG. 6 or FIG. 7. Alternatively, the host computer 02 may be the host computer shown in FIG. 8.

An embodiment of the present disclosure provides a non-volatile computer-readable storage medium storing instructions thereon, wherein the non-volatile computer-readable storage medium, when run on a computer, causes the computer to perform the setup method shown in FIG. 2 or FIG. 3 or the position detection method at the radiotherapy stage shown in FIG. 5.

In addition, the term "and/or" in the present disclosure merely describes an association relationship for describing associated objects and represents that three relationships may exist. For example, A and/or B may represent the following three cases: only A exists, both A and B exist, and only B exists.

The foregoing is merely optional embodiments of the present disclosure but is not used to limit the present disclosure. Any changes, equivalent replacements, and improvements made within the spirit and principle of the present disclosure shall fall within the protection scope of the present disclosure.

What is claimed is:

1. A setup method, comprising:
   acquiring, at a setup stage, a position of a reference mark point provided on a noninvasive positioning device in an infrared coordinate system of an infrared positioning system;
   according to the position of the reference mark point in the infrared coordinate system, a relative position between the reference mark point and an image center point in an electronic scanning image, and a position of an isocenter of a radiotherapy equipment in a patient supporting device PSD coordinate system of the radiotherapy equipment, determining a first offset between the image center point and the isocenter in the PSD coordinate system; and
   adjusting the first offset to a first target offset by adjusting a position of a patient supporting device in the PSD coordinate system.

2. The method according to claim 1, wherein determining the first offset between the image center point and the isocenter in the PSD coordinate system according to the position of the reference mark point in the infrared coordinate system, the relative position between the reference mark point and the image center point in the electronic scanning image, and the position of the isocenter of a radiotherapy equipment in the PSD coordinate system of the radiotherapy equipment comprises:
   determining the position of the image center point in the infrared coordinate system, according to the position of the reference mark point in the infrared coordinate system, and the relative position between the reference mark point and the image center point in the electronic scanning image; and
   determining the first offset between the image center point and the isocenter in the PSD coordinate system based on the position of the image center point in the infrared coordinate system, the position of the isocenter of the radiotherapy equipment in the PSD coordinate system of the radiotherapy equipment, and a conversion relationship between the infrared coordinate system and the PSD coordinate system.

3. The method according to claim 2, wherein determining the first offset between the image center point and the isocenter in the PSD coordinate system based on the position of the image center point in the infrared coordinate system, the position of the isocenter of the radiotherapy equipment in the PSD coordinate system of the radiotherapy equipment, and the conversion relationship between the infrared coordinate system and the PSD coordinate system comprises:

determining a position of the image center point in the PSD coordinate system according to the position of the image center point in the infrared coordinate system and the conversion relationship between the infrared coordinate system and the PSD coordinate system; and determining the first offset between the image center point and the isocenter in the PSD coordinate system based on the position of the image center point in the PSD coordinate system and the position of the isocenter in the PSD coordinate system.

4. The method according to claim 1, further comprising:

acquiring, at the setup stage, a position of a positioning mark point provided on a body surface of a patient in the infrared coordinate system;

determining a first relative position between the positioning mark point and the reference mark point in the infrared coordinate system;

determining a second offset between the first relative position and a standard position in the PSD coordinate system according to a conversion relationship between the infrared coordinate system and the PSD coordinate system, wherein the standard position is a relative position between the positioning mark point and the reference mark point in the electronic scanning image; and adjusting the second offset to a second target offset by adjusting the position of the patient supporting device in the PSD coordinate system.

5. The method according to claim 4, wherein a plurality of positioning mark points are provided on the body surface of the patient;

wherein determining the first relative position between the positioning mark point and the reference mark point in the infrared coordinate system comprises:

determining the respective first relative position between each of the positioning mark points and the reference mark point in the infrared coordinate system, and obtaining a plurality of first relative positions;

wherein determining the second offset between the first relative position and the standard position in the PSD coordinate system comprises:

determining the respective second offset between each of the first relative positions and the standard position in the PSD coordinate system according to the conversion relationship between the infrared coordinate system and the PSD coordinate system, and obtaining a plurality of second offsets; and wherein adjusting the second offset to the second target offset by adjusting the position of the patient supporting device comprises:

detecting each of the second offsets for whether it is within a target offset range; and when it is determined that a number of second offsets that are not within the target offset range is more than a number threshold, adjusting the second offsets to the second target offset by adjusting the position of the patient supporting device.

6. The method according to claim 1, wherein the noninvasive positioning device comprises a positioning mask and a positioning bracket for fixing the positioning mask; and wherein at least one reference mark point is provided on at least one of the positioning mask and the positioning bracket.

7. The method according to claim 1, wherein at least three reference mark points are provided on the noninvasive positioning device; and wherein among the at least three reference mark points, orthographic projections of any two reference mark points onto a first plane are not overlapped, the first plane being a plane defined by any two coordinate axes in the PSD coordinate system.

8. A data processing device, comprising: a memory, a processor, and a computer program stored in the memory and executable by the processor, wherein the computer program, when executed by the processor, is configured to cause the processor perform a method comprising:

acquiring, at a setup stage, a position of a reference mark point provided on a noninvasive positioning device in an infrared coordinate system of an infrared positioning system;

according to the position of the reference mark point in the infrared coordinate system, a relative position between the reference mark point and an image center point in an electronic scanning image, and a position of an isocenter of a radiotherapy equipment in a patient supporting device PSD coordinate system of the radiotherapy equipment, determining a first offset between the image center point and the isocenter in the PSD coordinate system; and adjusting the first offset to a first target offset by adjusting a position of a patient supporting device in the PSD coordinate system.

9. A radiotherapy system, comprising: an infrared positioning system, a patient supporting device, and the data processing device as defined in claim 8.

10. The data processing device according to claim 8, wherein determining the first offset between the image center point and the isocenter in the PSD coordinate system according to the position of the reference mark point in the infrared coordinate system, the relative position between the reference mark point and the image center point in the electronic scanning image, and the position of the isocenter of a radiotherapy equipment in the PSD coordinate system of the radiotherapy equipment comprises:

determining the position of the image center point in the infrared coordinate system, according to the position of the reference mark point in the infrared coordinate system, and the relative position between the reference mark point and the image center point in the electronic scanning image; and determining the first offset between the image center point and the isocenter in the PSD coordinate system based on the position of the image center point in the infrared coordinate system, the position of the isocenter of the radiotherapy equipment in the PSD coordinate system of the radiotherapy equipment, and a conversion relationship between the infrared coordinate system and the PSD coordinate system.

11. The data processing device according to claim 10, wherein determining the first offset between the image center point and the isocenter in the PSD coordinate system based on the position of the image center point in the infrared coordinate system, the position of the isocenter of the radiotherapy equipment in the PSD coordinate system of the radiotherapy equipment, and the conversion relationship between the infrared coordinate system and the PSD coordinate system comprises:

determining a position of the image center point in the PSD coordinate system according to the position of the image center point in the infrared coordinate system and the conversion relationship between the infrared coordinate system and the PSD coordinate system; and determining the first offset between the image center point and the isocenter in the PSD coordinate system based on the position of the image center point in the PSD coordinate system and the position of the isocenter in the PSD coordinate system.

12. The data processing device according to claim 8, wherein the method further comprises:
acquiring, at the setup stage, a position of a positioning mark point provided on a body surface of a patient in the infrared coordinate system;
determining a first relative position between the positioning mark point and the reference mark point in the infrared coordinate system;
determining a second offset between the first relative position and a standard position in the PSD coordinate system according to a conversion relationship between the infrared coordinate system and the PSD coordinate system, wherein the standard position is a relative position between the positioning mark point and the reference mark point in the electronic scanning image; and
adjusting the second offset to a second target offset by adjusting the position of the patient supporting device in the PSD coordinate system.

13. The data processing device according to claim 12, wherein a plurality of positioning mark points are provided on the body surface of the patient;
wherein determining the first relative position between the positioning mark point and the reference mark point in the infrared coordinate system comprises:
determining the respective first relative position between each of the positioning mark points and the reference mark point in the infrared coordinate system, and obtaining a plurality of first relative positions;
wherein determining the second offset between the first relative position and the standard position in the PSD coordinate system comprises:
determining the respective second offset between each of the first relative positions and the standard position in the PSD coordinate system according to the conversion relationship between the infrared coordinate system and the PSD coordinate system, and obtaining a plurality of second offsets; and
wherein adjusting the second offset to the second target offset by adjusting the position of the patient supporting device comprises:
detecting each of the second offsets for whether it is within a target offset range; and
when it is determined that a number of second offsets that are not within the target offset range is more than a number threshold, adjusting the second offsets to the second target offset by adjusting the position of the patient supporting device.

14. The data processing device according to claim 8, wherein the noninvasive positioning device comprises a positioning mask and a positioning bracket for fixing the positioning mask; and
wherein at least one reference mark point is provided on at least one of the positioning mask and the positioning bracket.

15. The data processing device according to claim 8, wherein at least three reference mark points are provided on the noninvasive positioning device; and
wherein among the at least three reference mark points, orthographic projections of any two reference mark points onto a first plane are not overlapped, the first plane being a plane defined by any two coordinate axes in the PSD coordinate system.

16. A non-volatile computer-readable storage medium storing instructions thereon, wherein the instructions, when run on a computer, cause the computer to perform a method comprising:
acquiring, at a setup stage, a position of a reference mark point provided on a noninvasive positioning device in an infrared coordinate system of an infrared positioning system;
according to the position of the reference mark point in the infrared coordinate system, a relative position between the reference mark point and an image center point in an electronic scanning image, and a position of an isocenter of a radiotherapy equipment in a patient supporting device PSD coordinate system of the radiotherapy equipment, determining a first offset between the image center point and the isocenter in the PSD coordinate system; and
adjusting the first offset to a first target offset by adjusting a position of a patient supporting device in the PSD coordinate system.

17. The non-volatile computer-readable storage medium according to claim 16, wherein determining the first offset between the image center point and the isocenter in the PSD coordinate system according to the position of the reference mark point in the infrared coordinate system, the relative position between the reference mark point and the image center point in the electronic scanning image, and the position of the isocenter of a radiotherapy equipment in the PSD coordinate system of the radiotherapy equipment comprises:
determining the position of the image center point in the infrared coordinate system, according to the position of the reference mark point in the infrared coordinate system, and the relative position between the reference mark point and the image center point in the electronic scanning image; and
determining the first offset between the image center point and the isocenter in the PSD coordinate system based on the position of the image center point in the infrared coordinate system, the position of the isocenter of the radiotherapy equipment in the PSD coordinate system of the radiotherapy equipment, and a conversion relationship between the infrared coordinate system and the PSD coordinate system.

18. The non-volatile computer-readable storage medium according to claim 17, wherein determining the first offset between the image center point and the isocenter in the PSD coordinate system based on the position of the image center point in the infrared coordinate system, the position of the isocenter of the radiotherapy equipment in the PSD coordinate system of the radiotherapy equipment, and the conversion relationship between the infrared coordinate system and the PSD coordinate system comprises:
determining a position of the image center point in the PSD coordinate system according to the position of the image center point in the infrared coordinate system and the conversion relationship between the infrared coordinate system and the PSD coordinate system; and
determining the first offset between the image center point and the isocenter in the PSD coordinate system based on the position of the image center point in the PSD coordinate system and the position of the isocenter in the PSD coordinate system.

19. The non-volatile computer-readable storage medium according to claim 16, wherein the method further comprises:
    acquiring, at the setup stage, a position of a positioning mark point provided on a body surface of a patient in the infrared coordinate system;
    determining a first relative position between the positioning mark point and the reference mark point in the infrared coordinate system;
    determining a second offset between the first relative position and a standard position in the PSD coordinate system according to a conversion relationship between the infrared coordinate system and the PSD coordinate system, wherein the standard position is a relative position between the positioning mark point and the reference mark point in the electronic scanning image; and
    adjusting the second offset to a second target offset by adjusting the position of the patient supporting device in the PSD coordinate system.

20. The non-volatile computer-readable storage medium according to claim 19, wherein a plurality of positioning mark points are provided on the body surface of the patient;
    wherein determining the first relative position between the positioning mark point and the reference mark point in the infrared coordinate system comprises:
        determining the respective first relative position between each of the positioning mark points and the reference mark point in the infrared coordinate system, and obtaining a plurality of first relative positions;
    wherein determining the second offset between the first relative position and the standard position in the PSD coordinate system comprises:
        determining the respective second offset between each of the first relative positions and the standard position in the PSD coordinate system according to the conversion relationship between the infrared coordinate system and the PSD coordinate system, and obtaining a plurality of second offsets; and
    wherein adjusting the second offset to the second target offset by adjusting the position of the patient supporting device comprises:
        detecting each of the second offsets for whether it is within a target offset range; and
        when it is determined that a number of second offsets that are not within the target offset range is more than a number threshold, adjusting the second offsets to the second target offset by adjusting the position of the patient supporting device.

* * * * *